(12) United States Patent
Belkowski et al.

(10) Patent No.: US 7,892,779 B2
(45) Date of Patent: Feb. 22, 2011

(54) METHOD OF DETERMINING CHYMASE ACTIVITY WITH SECRETORY LEUKOCYTE PROTEASE INHIBITOR

(75) Inventors: Stanley Belkowski, Norristown, PA (US); Michael R. D'Andrea, Cherry Hill, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 12/500,034

(22) Filed: Jul. 9, 2009

(65) Prior Publication Data

US 2009/0275068 A1 Nov. 5, 2009

Related U.S. Application Data

(62) Division of application No. 11/652,753, filed on Jan. 12, 2007, now Pat. No. 7,575,888.

(60) Provisional application No. 60/758,400, filed on Jan. 12, 2006.

(51) Int. Cl.
*C12Q 1/37* (2006.01)

(52) U.S. Cl. ........................................................ 435/23

(58) Field of Classification Search ................... 435/23, 435/69.2
See application file for complete search history.

(56) References Cited

U.S. PATENT DOCUMENTS

| | | | |
|---|---|---|---|
| 4,376,110 A | 3/1983 | David | |
| 4,486,530 A | 12/1984 | David | |
| 5,223,409 A | 6/1993 | Ladner | |
| 5,567,602 A | 10/1996 | Clark et al. | |
| 5,571,698 A | 11/1996 | Ladner | |
| 5,633,227 A | 5/1997 | Muller et al. | |
| 5,861,264 A | 1/1999 | Elrod et al. | |
| 7,247,704 B2 | 7/2007 | Barr | |
| 7,575,888 B2 * | 8/2009 | Belkowski et al. | ............ 435/23 |
| 2002/0010318 A1 | 1/2002 | Niven | |
| 2003/0195172 A1 | 10/2003 | Greco | |
| 2004/0110811 A1 | 6/2004 | Sakai | |
| 2005/0176769 A1 | 8/2005 | Hawkins | |

OTHER PUBLICATIONS

Westin U. et al. The Effect of Immediate Hypersensitivity Reactions . . . Allergy (Copenhagen) 54(8)857-865, 1999.*
Belkowski S. et al. Cleaved Secretory Leukocyte Protease Inhibitor . . . Clinical & Experimental Allergy 39(8)1179-1186, 2009.*
Pemberton, "Differential Inhibition of Mast Cell Chymases by Secretory Leukocyte Protease Inhibitor", Biochimica et Biophysica Acta., 1998, vol. 1379, pp. 29-34, abstract.
Grutter et al., Embo J 1988; 7:345-51.
Bitter et al., "Expression and Secretion Vectors for Yeast", Methods in Enzymology, (1987), vol. 153, pp. 516-544.
Cull et al., "Screening for Receptor Ligands Using Large Libraries of Peptides Linked to the C Terminus of the Lac Repressor", Proceedings of the National Academy of Sciences of the United States of America, (1992), vol. 89, pp. 1865-1869.
Dell'Italia et al., "Dissecting the Role of Chymase in Angiotensin II Formation and Heart and Blood Vessel Diseases", Current Opinion in Cardiology, (2003) vol. 17, issue 5, pp. 374-379.
Doggrell et al., "Cardiac Chymase: Pathophysiological Role and Therapeutic Potential of Chymase Inhibitors", Canadian Journal of Physiology and Pharmacology, (2005), vol. 83, issue 2, pp. 123-130.
Fink et al., "Inhibition of Mast Cell Chymase by Eglin c and Antileukoprotease (HUSI-I). Indications for Potential Biological Functions of these Inhibitors", Biological Chemistry, Hoppe-Seyler, (1986), vol. 367, issue 7, pp. 567-571.
Fodor, "Multiplexed Biochemical Assays with Biological Chips", Nature, (1993), vol. 364, pp. 555-556.
Fryksmark et al., "Distribution of Antileukoprotease in Upper Respiratory Mucosa, The Annals of Otology", Rhinology Laryngology, (1982), vol. 91, issue 3, part 1, pp. 268-271.
Garavilla et al., "A Novel, Potent Dual Inhibitor of the Leukocyte Proteases Cathepsin G and Chymase", Biochemistry (Easton), (2005), vol. 280, pp. 18001-18007.
Gordon et al., "Applications of Combinatorial Technologies to Drug Discovery. 2. Combinatorial Organic Synthesis, Library Screening Strategies, and Future Directions", Journal of Medicinal Chemistry, (1994), vol. 37, issue 10, pp. 1385-1401.
Grutter et al., "The 2.5 A X-ray Crystal Structure of the Acid-Stable Proteinase Inhibitor from Human Mucous Secretions Analysed in it Complex with Bovine Alpha-Chymotrypsin", The EMBO Journal, (1988); vol. 7, issue 2, pp. 345-351.
Houghten et al., "The Use of Synthetic Peptide Combinatorial Libraries for the Identification of Bioactive Peptides", BioTechniques, (1992), vol. 13, issue 3, pp. 412-421.
Huang et al., "Chymase is Upregulated in Diabetic Nephropathy: Implications for an Alternative Pathway of Angiotensin II-mediated Diabetic Renal and Vascular Disease", Journal of the American Society of Nephrology, (2003), vol. 14, issue 7, pp. 1738-1747.
Kanazawa et al., "A Case-Control Study of Bronchial Asthma Associated with Ulcerative Colitis: Role of Airway Microvascular Permeability", Clinical & Experimental Allergy, (2005), vol. 35, issue 11, pp. 1432-1436.
Kobayashi et al., "Mast Cells as a Target of Rheumatoid Arthritis Treatment", Japanese Journal of Pharmacology, (2002) vol. 90, issue 1, pp. 7-11.
Kramps et al., "Localization of Low Molecular Weight Protease Inhibitor in Serous Secretory Cells of the Respiratory Tract", The Journal of Histochemistry and Cytochemistry, (1981), vol. 29, issue 6, pp. 712-719.
Kramps et al., "ELISA for Quantitative Measurement of Low-Molecular-Weight Bronchial Protease Inhibitor in Human Sputum", The American Review of Respiratory Disease, (1984), vol. 129, issue 6, pp. 959-963.

(Continued)

Primary Examiner—Ralph Gitomer (57) ABSTRACT

It is now discovered that human chymase cleaves human SLPI at a specific site and that this cleavage can be used as an indicator of chymase activity. The present invention provides methods of diagnosing a chymase-associated disease or evaluating the efficiency of a treatment of a chymase-associated disease in a human subject by measuring SLPI processing, as well as other related methods and compositions.

15 Claims, 6 Drawing Sheets

OTHER PUBLICATIONS

Lam, "Application of Combinatorial Library Methods in Cancer Research and Drug Discovery", Anticancer Drug Design, (1997), vol. 12, pp. 145-167.

Lam, "A New Type of Synthetic Peptide Library for Identifying Ligand-Binding Activity", Nature, (1991), vol. 354, pp. 82-84.

Lee et al., "Distribution of Secretory Leukoprotease Inhibitor in the Human Nasal Airway", The American Review of Respiratory Disease, (1993), vol. 147, issue 3, pp. 710-716.

Mooren et al., "Ultrastructural Localization of the Low Molecular Weight Protease Inhibitor in Human Bronchial Glands", The Journal of Histochemistry and Cytochemistry, (1982), vol. 30, issue 11, pp. 1130-1134.

Muto et al., "Recent Chymase Inhibitors and Their Effects in in Vivo Models", IDrugs: The Investigational Drugs Journal, (2002), vol. 5, issue 12, pp. 1141-1150.

Needleman & Wunsch, "A General Method Applicable to the Search for Similarities in the Amino Acid Sequence of Two Protein", Journal of Molecular Biology, (1970) vol. 48, pp. 443-453.

Ota et al., "The Expression of Secretory Leukocyte Protease Inhibitor (SLPI) in the Fallopian Tube: SLPI Protects the acrosome Reaction of Sperm for Inhibitory Effects of Elastase", Human Reproduction, (2002), vol. 17, issue 10, pp. 2517-2522.

Pemberton et al., "Differential Inhibition of Mast Cell Chymase by Secretory Leukocyte Protease Inhibitor", Biochimica et Biophysica Acta, (1998); vol. 1379, issue 1, pp. 29-34.

Vogelmeier, "Anti-Neutrophil Elastase Defense of the Normal Human Respiratory Epithelial Surface Provided by the Secretory Leukoprotese Inhibitor", The Journal of Clinical Investigation (1991), vol. 87, pp. 482-488.

Scott and Smith, "Searching for Peptide Ligands with an Epitope Library", Science, (1990), vol. 249, issue 4967, pp. 386-390.

Takai et al., "Inhibition of Chymase Reduces Vascular Proliferation in Dog Grafted Veins", FEBS Letters, (2000), vol. 467, issue 2-3, pp. 141-144.

Thompson et al., "Isolation, Properties, and Complete Amino Acid Sequence of Human Secretory Leukocyte Protease Inhibitor, a Potent Inhibitor of Leukocyte Elastase", Proceedings of the National Academy of Sciences of the United States of America, (1986), vol. 83, issue 18, pp. 6692-6696.

Walter et al., "Inhibition of Human Mast Cell Chymase by Secretory Leukocyte Proteinase Inhibitor: Enhancement of the Interaction by Heparin", Archives of Biochemistry and Biophysics, (1996), vol. 327, issue 1, pp. 81-88.

Westin et al., "Identification of SLPI (Secretory Leukocyte Protease Inhibitor) in Human Mast Cells Using Immunohistochemistry and in Situ Hybridisation", Biological Chemistry, (1999), vol. 380, issue 4, pp. 489-493.

Willems et al., "Antileukoprotease-Containing Bronchiolar Cells. Relationship with Morphologic Disease of Small Airways and Parenchyma", The American Review of Respiratory Disease, (1989), vol. 139, issue 5, pp. 1244-1250.

Zuckermann et al., "Discovery of Nanomolar Ligands for 7-Transmembrane G-Protein-Coupled Receptors from a Diverse N-(Substituted) Glycine Peptoid Library", Journal of Medicinal Chemistry, (1994), vol. 37, pp. 2678-2685.

* cited by examiner

SEQUENCE LISTING

```
<160> NUMBER OF SEQ ID NOS: 4

<210> SEQ ID NO 1
<211> LENGTH: 247
<212> TYPE: PRT
<213> ORGANISM: Homo sapiens

<400> SEQUENCE: 1

Met Leu Leu Leu Pro Leu Pro Leu Leu Leu Phe Leu Leu Cys Ser Arg
1               5                   10                  15

Ala Glu Ala Gly Glu Ile Ile Gly Gly Thr Glu Cys Lys Pro His Ser
            20                  25                  30

Arg Pro Tyr Met Ala Tyr Leu Glu Ile Val Thr Ser Asn Gly Pro Ser
        35                  40                  45

Lys Phe Cys Gly Gly Phe Leu Ile Arg Arg Asn Phe Val Leu Thr Ala
    50                  55                  60

Ala His Cys Ala Gly Arg Ser Ile Thr Val Thr Leu Gly Ala His Asn
65                  70                  75                  80

Ile Thr Glu Glu Glu Asp Thr Trp Gln Lys Leu Glu Val Ile Lys Gln
                85                  90                  95
```

```
Phe Arg His Pro Lys Tyr Asn Thr Ser Thr Leu His His Asp Ile Met
                100                 105                 110
Leu Leu Lys Leu Lys Glu Lys Ala Ser Leu Thr Leu Ala Val Gly Thr
            115                 120                 125
Leu Pro Phe Pro Ser Gln Phe Asn Phe Val Pro Pro Gly Arg Met Cys
        130                 135                 140
Arg Val Ala Gly Trp Gly Arg Thr Gly Val Leu Lys Pro Gly Ser Asp
145                 150                 155                 160
Thr Leu Gln Glu Val Lys Leu Arg Leu Met Asp Pro Gln Ala Cys Ser
                165                 170                 175
His Phe Arg Asp Phe Asp His Asn Leu Gln Leu Cys Val Gly Asn Pro
            180                 185                 190
Arg Lys Thr Lys Ser Ala Phe Lys Gly Asp Ser Gly Gly Pro Leu Leu
        195                 200                 205
Cys Ala Gly Val Ala Gln Gly Ile Val Ser Tyr Gly Arg Ser Asp Ala
210                 215                 220
Lys Pro Pro Ala Val Phe Thr Arg Ile Ser His Tyr Arg Pro Trp Ile
225                 230                 235                 240
Asn Gln Ile Leu Gln Ala Asn
                245

<210> SEQ ID NO 2
<211> LENGTH: 107
<212> TYPE: PRT
<213> ORGANISM: Homo sapiens

<400> SEQUENCE: 2

Ser Gly Lys Ser Phe Lys Ala Gly Val Cys Pro Pro Lys Lys Ser Ala
1               5                   10                  15
Gln Cys Leu Arg Tyr Lys Lys Pro Glu Cys Gln Ser Asp Trp Gln Cys
                20                  25                  30
Pro Gly Lys Lys Arg Cys Cys Pro Asp Thr Cys Gly Ile Lys Cys Leu
            35                  40                  45
Asp Pro Val Asp Thr Pro Asn Pro Thr Arg Arg Lys Pro Gly Lys Cys
        50                  55                  60
Pro Val Thr Tyr Gly Gln Cys Leu Met Leu Asn Pro Pro Asn Phe Cys
65                  70                  75                  80
Glu Met Asp Gly Gln Cys Lys Arg Asp Leu Lys Cys Cys Met Gly Met
                85                  90                  95
Cys Gly Lys Ser Cys Val Ser Pro Val Lys Ala
            100                 105

<210> SEQ ID NO 3
<211> LENGTH: 72
<212> TYPE: PRT
<213> ORGANISM: Homo sapiens

<400> SEQUENCE: 3

Ser Gly Lys Ser Phe Lys Ala Gly Val Cys Pro Pro Lys Lys Ser Ala
1               5                   10                  15
Gln Cys Leu Arg Tyr Lys Lys Pro Glu Cys Gln Ser Asp Trp Gln Cys
                20                  25                  30
Pro Gly Lys Lys Arg Cys Cys Pro Asp Thr Cys Gly Ile Lys Cys Leu
            35                  40                  45
Asp Pro Val Asp Thr Pro Asn Pro Thr Arg Arg Lys Pro Gly Lys Cys
        50                  55                  60
```

```
Pro Val Thr Tyr Gly Gln Cys Leu
65                  70

<210> SEQ ID NO 4
<211> LENGTH: 35
<212> TYPE: PRT
<213> ORGANISM: Homo sapiens

<400> SEQUENCE: 4

Met Leu Asn Pro Pro Asn Phe Cys Glu Met Asp Gly Gln Cys Lys Arg
1               5                   10                  15

Asp Leu Lys Cys Cys Met Gly Met Cys Gly Lys Ser Cys Val Ser Pro
            20                  25                  30

Val Lys Ala
        35
```

METHOD OF DETERMINING CHYMASE ACTIVITY WITH SECRETORY LEUKOCYTE PROTEASE INHIBITOR

CROSS-REFERENCE TO RELATED APPLICATIONS

This application is a divisional filing of U.S. Ser. No. 11/652,753, filed on Jan. 12, 2007 now U.S. Pat. No. 7,575,888 and claims priority to U.S. Ser. No. 60/758,400 filed on Jan. 12, 2006, the entire contents of which are incorporated by reference herein.

FIELD OF THE INVENTION

The present invention relates to methods of analyzing chymase activity. In particular, the invention relates to diagnosing a chymase-associated disease or evaluating the efficiency of a treatment of a chymase-associated disease in a human subject by measuring SLPI processing.

BACKGROUND OF THE INVENTION

Secretory Leukocyte Protease Inhibitor (SLPI) was first discovered as an 11.7 kD inhibitor for elastase and cathepsin G (Thompson et al., *Proc Natl Acad Sci USA* 1986; 83:6692-6). SLPI is expressed by mast cells (Westin et al., *Biol Chem* 1999; 380:489-93) and is present in the mucosa of the upper airway (Fryksmark et al., *Ann Otol Rhinol Laryngol* 1982; 91:268-71) and sputum (Kramps et al., *J Histochem Cytochem* 1981; 29:712-9). High amounts of SLPI have been measured in the nasal (Lee et al., *Am Rev Respir Dis* 1993; 147:710-6), trachea and broncus (Kramps et al., *Am Rev Respir Dis* 1984; 129:959-63; Mooren et al., *J Histochem Cytochem* 1982; 30:1130-4), maxillary sinus (Fryksmark et al., supra) and goblet cells of the bronchiole epithelium (Willems et al., Am Rev Respir Dis 1989; 139:1244-50).

The crystallography studies of SLPI have shown the molecule to be a member of the Whey Acidic protein-like family (Grutter et al., *Embo J* 1988; 7:345-51). These proteins have two 4 disulfide linked domains. The 4 disulfide linkages and helical structure of each domain make SLPI a very stable protein. Bovine (Grutter supra) and sheep (Pemberton et al., *Biochim Biophys Acta* 1998; 1379:29-34) mast cell proteases have been shown to cleave SLPI at Leu72-Met73. Others have shown a lower molecular weight processed product of SLPI but have not characterized the enzyme responsible for this cleavage (Ota et al., *Hum Reprod* 2002; 17:2517-22). SLPI was described as the most effective inhibitor for chymase (Walter et al., *Arch Biochem Biophys* 1996; 327:81-8; and Fink et al., *Biol Chem Hoppe Seyler* 1986; 367:567-71).

Chymase is a chymotryptic serine proteinase that belongs to the peptidase family S1. It is expressed in mast cells and globule leucocytes of skin and lung and thought to function in the degradation of the extracellular matrix, the regulation of submucosal gland secretion, and the generation of vasoactive peptides. It has a maximal activity immediately upon release into the extracellular matrix after mast cells have been activated (Takai et al., *FEBS Lett* 467: 141-144, 2000). There are two forms of mammalian chymase, α and β, which differ in species and have different functions. In human and baboons, only α-chymase is found, while dogs, rats, and mice have both α- and β-chymases (Dell'Italia et al., *Curr Opin Cardiol* 2003 17: 374-379).

Although the precise patho-physiological roles of chymase have yet to be determined, chymase has been implicated in microvascular leakage, neutrophil accumulation, the stimulation of mucus secretion, and the modulation of cytokines, etc. A potent, chymase-selective inhibitor may be indicated in mast cell-mediated diseases such as asthma, pulmonary inflammation, and chronic obstructive pulmonary diseases (COPD). Because chymase can play a role in the generation of cardiac and vascular wall angiotensin II, a chymase inhibitor may have potential use as an antihypertensive treatment for vascular wall injury and inflammation (atherosclerosis/restenosis), as well as cardiac hypertrophy. Chymase is a target for cardiovascular disease therapies (Doggrell et al., Can J Physiol Pharmacol. 2005 February; 83(2):123-30). In addition, chymase has also been proposed to play a critical role in diseases such as rheumatoid arthritis (Kobayashi et al., *Jpn J Pharmacol.* 2002 September; 90(1):7-11), diabetic nephropathy (Huang et al., *J Am Soc Nephrol.* 2003 July; 14(7):1738-47), and inflammatory diseases (Muto et al., *Idrugs.*, 2002, 12, 1141-50)

Therefore, compounds designed to inhibit the biological activity of chymase may offer therapeutic benefit in a number of disease areas. Selective chymase inhibitors have been developed, which include TY-51076, SUN-C8257, BCEAB, NK320, and TEI-E548 (see Doggrell et al supra). Promising results have been obtained with these chymase inhibitors in animal models of myocardial infarction, cardiomyopathy, and tachycardia-induced heart failure. To facilitate the test of chymase inhibitors in human, as well as the study of chymase activity in human in general, there is a need to develop a biomarker for chymase activity in human.

SUMMARY OF THE INVENTION

It is now discovered that human chymase cleaves human SLPI at a specific site and that this cleavage can be used as an indicator of chymase activity. This cleavage is specific to chymase when tested over a series of proteases known to interact with SLPI including tryptase, cathepsin G, elastase and proteinase 3.

In one general aspect, the present invention provides a method of detecting a chymase-associated disease in a human subject, comprising the steps of: a) obtaining a biological sample from the human subject; b) measuring the level of human SLPI cleavage by human chymase in the biological sample; and c) comparing the level measured from step b) to a control of the level of human SLPI cleavage by human chymase in a healthy human subject, wherein an elevated level of human SLPI cleavage by human chymase compared to said control indicates that the human subject has a chymase-associated disease or has increased risk of a chymase-associated disease.

In another general aspect, the present invention provides a method of evaluating the effectiveness of a treatment to a chymase-associated disease in a human patient, comprising the steps of: a) obtaining a biological sample from the human patient; b) measuring the level of human SLPI cleavage by human chymase in the biological sample; and c) comparing the level measured from step b) to a control of the level of human SLPI cleavage by human chymase in the human patient prior to the treatment, wherein a decreased level of human SLPI cleavage by human chymase compared to said control indicates that the treatment to a chymase-associated disease in said patient is effective.

The present invention also provides a method of measuring the biological activity of a human chymase, comprising the steps of: a) contacting the human chymase with a human SLPI in an assay mixture; b) incubating the assay mixture under a condition wherein the human chymase cleaves the human SLPI; and c) measuring the level of human SLPI cleavage by human chymase in the assay mixture.

The present invention further provides a method of identifying a compound that decreases the biological activity of a human chymase comprising the steps of: a) contacting a test compound with a human chymase and a human SLPI in an assay mixture; b) incubating the assay mixture under a condition wherein the human chymase cleaves the human SLPI; c) measuring the level of human SLPI cleavage by human chymase in the assay mixture; and d) comparing the level detected from step c) to that detected from a control wherein the test compound is omitted from the assay mixture.

In addition, the present invention also provides kits related to the methods of the present invention.

Another aspect of the present invention is a method of classifying a patient who has a better chance to respond to a treatment involving a chymase inhibitor, comprising the steps of a) obtaining a biological sample from a patient; b) measuring the level of human SLPI cleavage by human chymase in the biological sample; and c) comparing the level measured from step b) to a control of the level of human SLPI cleavage by human chymase in a healthy human subject, wherein an elevated level of human SLPI cleavage by human chymase compared to said control indicates that the patient has a better chance to respond to a treatment involving a chymase inhibitor.

Other aspects, features and advantages of the invention will be apparent from the following disclosure, including the detailed description of the invention and its preferred embodiments and the appended claims.

DESCRIPTION OF THE FIGURES

FIG. 5 illustrates that an increase in cSLPI correlates with increase in allergic symptoms. cSLPI to total SLPI ratios were determined in nasal lavages by western analysis obtained from individuals 0.75 hours and 0.5 hours prior to antigenic challenge and 0.5 hours and 7 hours post antigen challenge (FIG. 5b). Patients were scored for symptom intensity (Lebel score) at the same time points (FIG. 5a).

DETAILED DESCRIPTION

All publications cited herein are hereby incorporated by reference. Unless defined otherwise, all technical and scientific terms used herein have the same meaning as commonly understood to one of ordinary skill in the art to which this invention pertains.

As used herein, the terms "comprising", "containing", "having" and "including" are used in their open, non-limiting sense.

The following are abbreviations that are at times used in this specification:
bp=base pair
cDNA=complementary DNA
COPD=chronic obstructive pulmonary disease
ELISA=enzyme-linked immunoabsorbent assay;
kb=kilobase; 1000 base pairs
PAGE=polyacrylamide gel electrophoresis
PCR=polymerase chain reaction
SDS=sodium dodecyl sulfate
SLPI=Secretory Leukocyte Protease Inhibitor As used herein, the term "biological activity of a chymase" refers to an activity exerted by the chymase as determined in vivo or in vitro, according to standard techniques. Exemplary biological activities of a chymase, include, but are not limited to, its ability to convert angiotensin I to the vasoactive peptide angiotensin II, to selectively convert big endothelin 1 to the 31 amino acid length peptide endothelin 1, to degrade the extracellular matrix, to cleave stem cell factor to yield a bioactive, soluble product, to process procollagenase, inflammatory cytokines and other bioactive peptides, including SLPI as described herein, etc.

A "biological sample" as used herein refers to a sample containing or consisting of cell or tissue matter, such as cells or biological fluids isolated from a subject. The "subject" can be a mammal, such as a rat, a mouse, a monkey, or a human, that has been the object of treatment, observation or experiment. Examples of biological samples include, for example, sputum, blood, blood cells (e.g., white blood cells), amniotic fluid, plasma, semen, saliva, bone marrow, tissue or fine-needle biopsy samples, urine, peritoneal fluid, pleural fluid, and cell cultures. Biological samples may also include sections of tissues such as frozen sections taken for histological purposes. A test biological sample is the biological sample that has been the object of analysis, monitoring, or observation. A control biological sample can be either a positive or a negative control for the test biological sample. Often, the control biological sample contains the same type of tissues, cells and/or biological fluids of interest as that of the test biological sample. In particular embodiments, the biological sample is a "clinical sample," which is a sample derived from a human patient.

A "cell" refers to at least one cell or a plurality of cells appropriate for the sensitivity of the detection method. The cell can be present in a cultivated cell culture. The cell can also be present in its natural environment, such as a biological tissue or fluid. Cells suitable for the present invention may be bacterial, but are preferably eukaryotic, and are most preferably mammalian.

A "human chymase" as used herein refers to a chymase that was originally isolated from a human. Chymase is a chymotryptic serine proteinase that belongs to the peptidase family S1. The synonyms of chymase include mast cell protease I; skeletal muscle protease; skin chymotryptic proteinase; mast cell serine proteinase, chymase; and skeletal muscle (SK) protease. Preferential cleavage for a chymase is: Phe-|-Xaa>Tyr-|-Xaa>Trp-|-Xaa>Leu-|-Xaa. An exemplary "human chymase" has the amino acid sequence of SEQ ID NO:1, which is depicted in GenBank protein ID: NP_001827. A "human chymase" as used herein includes structural and functional polymorphisms of the human chymase depicted in SEQ ID NO:1. "Polymorphism" refers to a set of genetic variants at a particular genetic locus among individuals in a population.

A "chymase-associated disease" or a "chymase-associated disorder" as used herein refers to a disease or disorder associated with over activity or over expression of chymase, or a disease or disorder that can be treated or ameliorated by decreasing the biological activity of chymase or by decreasing the amount of chymase in a subject, and subclinical manifestations or conditions that accompany with such a disease or disorder in the subject. Exemplary "chymase-associated diseases" include, but are not limited to asthma, allergic rhinitis, fibrosis, hypertension, cardiac hypertrophy, heart failure, rheumatoid arthritis, diabetic nephropathy, chronic obstructive pulmonary disease (COPD) and inflammatory diseases.

A "human SLPI" as used herein refers to a secretory leukocyte peptidase inhibitor that was originally isolated from a human. The synonyms of SLPI include ALP; MPI; ALK1; BLPI; HUSI; WAP4; WFDC4; and HUSI-I. SLPI protects epithelial tissues from serine proteases. It is found in various secretions including seminal plasma, cervical mucus, and bronchial secretions, and has affinity for trypsin, leukocyte elastase, and cathepsin G. Its inhibitory effect contributes to the immune response by protecting epithelial surfaces from attack by endogenous proteolytic enzymes; the protein is also thought to have broad-spectrum antibiotic activity. An exemplary "human SLPI" has the amino acid sequence of SEQ ID NO:2, which is the mature portion of the protein depicted in GenBank protein ID: NP_003055. A "human SLPI" as used herein includes structural and functional polymorphisms of the human SLPI depicted in SEQ ID NO:2.

The "level of human SLPI cleavage by human chymase" refers to the degree or the amount of human SLPI cleavage or proteolysis by human chymase. As used herein, the "level of human SLPI cleavage by human chymase" can be measured as the ratio of the human SLPI fragment resulting from chymase cleavage to the full length SLPI present in the test biological sample or assay mixture.

The "human SLPI fragment resulting from chymase cleavage" refers to a portion of a human SLPI that is produced from the proteolysis or cleavage of the SLPI by a chymase. It is discovered in this invention that a human chymase cleaves a human SLPI in between Leu72-Met73, wherein the number 72 or 73, refers to the position of the amino acid residue counting from the amino-terminal end of the human SLPI. Thus, an exemplary "human SLPI fragment resulting from a chymase cleavage" can be the Ser1-Leu72 or Met 73-Ala107 fragment of SEQ ID NO:2, which consists the amino acid sequence of SEQ ID NO:3 or SEQ ID NO:4, respectively. A "human SLPI fragment resulting from a chymase cleavage" as used herein includes structural and functional polymorphisms of the human SLPI fragment depicted in SEQ ID NO:3 or SEQ ID NO:4.

"Nucleotide sequence" refers to the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs of the natural nucleotides.

An "isolated" nucleic acid molecule is one that is substantially separated from at least one of the other nucleic acid molecules present in the natural source of the nucleic acid, or is substantially free of at least one of the chemical precursors or other chemicals when the nucleic acid molecule is chemically synthesized. An "isolated" nucleic acid molecule can also be, for example, a nucleic acid molecule that is substantially free of at least one of the nucleotide sequences that naturally flank the nucleic acid molecule at its 5' and 3' ends in the genomic DNA of the organism from which the nucleic acid is derived. A nucleic acid molecule is "substantially separated from" or "substantially free of" other nucleic acid molecule(s) or other chemical(s) in preparations of the nucleic acid molecule when there is less than about 30%, 20%, 10%, or 5% (by dry weight) of the other nucleic acid molecule(s) or the other chemical(s) (also referred to herein as a "contaminating nucleic acid molecule" or a "contaminating chemical").

Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

The term "oligonucleotide" or "oligo" refers to a single-stranded DNA or RNA sequence of a relatively short length, for example, less than 100 residues long. For many methods, oligonucleotides of about 16-25 nucleotides in length are useful, although longer oligonucleotides of greater than about 25 nucleotides may sometimes be utilized. Some oligonucleotides can be used as "primers" for the synthesis of complimentary nucleic acid strands. For example, DNA primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by the codons of genes may also be included in a polypeptide.

An "isolated protein" is one that is substantially separated from at least one of the other proteins present in the natural source of the protein, or is substantially free of at least one of the chemical precursors or other chemicals when the protein is chemically synthesized. A protein is "substantially separated from" or "substantially free of" other protein(s) or other chemical(s) in preparations of the protein when there is less than about 30%, 20%, 10%, or 5% (by dry weight) of the other protein(s) or the other chemical(s) (also referred to herein as a "contaminating protein" or a "contaminating chemical").

Isolated proteins can have several different physical forms. The isolated protein can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. A fragment, or physical association of fragments can have the biological activity associated with the full-length polypeptide; however, the degree of biological activity associated with individual fragments can vary.

An isolated polypeptide can be a non-naturally occurring polypeptide. For example, an "isolated polypeptide" can be a "hybrid polypeptide." An "isolated polypeptide" can also be a polypeptide derived from a naturally occurring polypeptide by additions or deletions or substitutions of amino acids. An isolated polypeptide can also be a "purified polypeptide" which is used herein to mean a specified polypeptide in a substantially homogeneous preparation substantially free of other cellular components, other polypeptides, viral materials, or culture medium, or when the polypeptide is chemically synthesized, chemical precursors or by-products associated with the chemical synthesis. A "purified polypeptide" can be obtained from natural or recombinant host cells by standard purification techniques, or by chemical synthesis, as will be apparent to skilled artisans.

The terms "hybrid protein," "hybrid polypeptide," "hybrid peptide," "fusion protein," "fusion polypeptide," and "fusion peptide" are used herein interchangeably to mean a non-naturally-occurring polypeptide or isolated polypeptide having a specified polypeptide molecule covalently linked to one or more other polypeptide molecules that do not link to the specified polypeptide in nature. Thus, a "hybrid protein" can be two naturally occurring proteins or fragments thereof linked together by a covalent linkage. A "hybrid protein" can also be a protein formed by covalently linking two artificial polypeptides together. Typically but not necessarily, the two or more polypeptide molecules are linked or "fused" together by a peptide bond forming a single non-branched polypeptide chain. The term "protein fragment" as used herein means a polypeptide that represents a portion of a protein.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation.

A "recombinant host cell" is a cell that has had introduced into it a recombinant DNA sequence. Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila*- and silkworm-derived cell lines. It is further understood that the term "recombinant host cell" refers not only to the particular subject cell, but also to the progeny or potential progeny of such a cell. Because certain modifications can occur in succeeding generations due to either mutation or environmental influences, such progeny may not, in fact, be identical to the parent cell, but are still included within the scope of the term as used herein.

"Sequence" means the linear order in which monomers occur in a polymer, for example, the order of amino acids in a polypeptide or the order of nucleotides in a polynucleotide.

"Sequence identity or similarity", as known in the art, is the relationship between two or more polypeptide sequences or two or more polynucleotide sequences, as determined by comparing the sequences. As used herein, "identity", in the context of the relationship between two or more nucleic acid sequences or two or more polypeptide sequences, refers to the percentage of nucleotide or amino acid residues, respectively, that are the same when the sequences are optimally aligned and analyzed. For purposes of comparing a queried sequence against, for example, the amino acid sequence SEQ ID NO:2, the queried sequence is optimally aligned with SEQ ID NO: 2 and the best local alignment over the entire length of SEQ ID NO:2 is obtained.

Analysis can be carried out manually or using sequence comparison algorithms. For sequence comparison, typically one sequence acts as a reference sequence, to which a queried sequence is compared. When using a sequence comparison algorithm, test and reference sequences are input into a computer, sub-sequence coordinates are designated, if necessary, and sequence algorithm program parameters are designated.

Optimal alignment of sequences for comparison can be conducted, for example, by using the homology alignment algorithm of Needleman & Wunsch, J Mol. Biol., 48:443 (1970). Software for performing Needleman & Wunsch analyses is publicly available through the Institut Pasteur (France) Biological Software website: http://bioweb.pasteur.fr/seqanal/interfaces/needle.html. The NEEDLE program uses the Needleman-Wunsch global alignment algorithm to find the optimum alignment (including gaps) of two sequences when considering their entire length. The identity is calculated along with the percentage of identical matches between the two sequences over the reported aligned region, including any gaps in the length. Similarity scores are also provided wherein the similarity is calculated as the percentage of matches between the two sequences over the reported aligned region, including any gaps in the length. Standard comparisons utilize the EBLOSUM62 matrix for protein sequences and the EDNAFULL matrix for nucleotide sequences. The gap open penalty is the score taken away when a gap is created; the default setting using the gap open penalty is 10.0. For gap extension, a penalty is added to the standard gap penalty for each base or residue in the gap; the default setting is 0.5.

Hybridization can also be used as a test to indicate that two polynucleotides are substantially identical to each other. Polynucleotides that share a high degree of identity will hybridize to each other under stringent hybridization conditions. "Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprises hybridization in 6× sodium chloride/sodium citrate (SSC) at about 45° C., followed by one or more washes in 0.2×SSC and 0.1% SDS at 50-65° C., depending upon the length over which the hybridizing polynucleotides share complementarity.

"Vector" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

In practicing the present invention, many conventional techniques in molecular biology, microbiology and recombinant DNA are used. These techniques are well-known and are explained in, for example, Current Protocols in Molecular Biology, Vols. I, II, and III, F. M. Ausubel, ed. (1997); and Sambrook et al., Molecular Cloning: A Laboratory Manual, Cold Spring Harbor Laboratory Press, Cold Spring Harbor, N.Y. (2001).

The invention provides a general method of measuring the biological activity of a human chymase by measuring the level of human SLPI cleavage by human chymase.

In one general aspect, the present invention provides a method of detecting a chymase-associated disease in a human subject by measuring the level of human SLPI cleavage by human chymase in a biological sample. A human subject who has a chymase-associated disease can have an overactive chymase or an increased level of chymase. Thus, a biological sample taken from such a human subject can contain more cleavage of SLPI at the specific site Leu72-Met73 by chymase as compared to that of a healthy human subject.

Any type of biological samples can be used in the invention. In particular embodiments, the biological samples can be saliva, sputum, nasal exudate, ELF or lavage fluids. The biological samples can be obtained from the human subject in ways known to a person skilled in the art. Control biological sample contains the same type of tissues, cells and/or biological fluids of interest as that of the test biological sample and can be obtained from one or a population of healthy humans who have not been diagnosed with a chymase-associated disease.

Both the level of the full length human SLPI and the level of the SLPI fragment resulting from chymase cleavage can be measured from the biological sample and used to quantify the level of human SLPI cleavage by human chymase. The level of the full length human SLPI and the level of the SLPI fragment resulting from a chymase cleavage in a biological sample can be measured by any means for protein quantification known to a person skilled in the art.

In one embodiment, the SLPI or SLPI fragment can be isolated or purified from a biological sample and the amount thereof determined. The SLPI or SLPI fragment can be readily separated from the rest of the biological sample using methods known in the art, e.g., size-based separation methods such as gel filtration. Additionally, after reduction of the sample the SLPI or SLPI fragment in a sample can be separated in a gel such as polyacrylamide gel and subsequently immunoblotted using an antibody immunoreactive with the protein complex.

Alternatively, the level of the SLPI or SLPI fragment can be determined in a biological sample without separation, isolation or purification. For this purpose, it is preferred that an antibody selectively immunoreactive with the SLPI or SLPI fragment is used in an immunoassay. For example, immunocytochemical methods can be used. Other well known antibody-based techniques can also be used including, e.g., enzyme-linked immunosorbent assay (ELISA), radioimmunoassay (RIA), immunoradiometric assays (IRMA), fluorescent immunoassays, protein A immunoassays, and immunoenzymatic assays (EMA). See e.g., U.S. Pat. Nos. 4,376,110 and 4,486,530, both of which are incorporated herein by reference.

The level of human SLPI cleavage by human chymase is then calculated as the ratio of the human SLPI fragment resulting from chymase cleavage to the full length SLPI present in the test biological sample or assay mixture. An elevated level of human SLPI cleavage by human chymase in the test sample compared to the control sample indicates that the human subject has a chymase-associated disease or has an increased risk of developing a chymase-associated disease.

In another general aspect, the present invention provides a method of evaluating the effectiveness of a treatment to a chymase-associated disease in a human patient by measuring the level of human SLPI cleavage by human chymase before, during or after the treatment. An effective treatment to a chymase-associated disease would decrease the biological activity of chymase or decrease the amount of chymase in the human patient. Thus, less cleavage of human SLPI at the specific site Leu72-Met73 by chymase would be observed in a biological sample taken from such a human patient after the effective treatment. As a control, biological sample containing the same type of tissues, cells and/or biological fluids of interest as that of the test biological sample can be obtained from the same human patient prior to the treatment. A decreased level of human SLPI cleavage by human chymase in the test sample compared to the control sample indicates that the treatment to a chymase-associated disease in said patient is effective.

The methods of the invention further comprise the step of analyzing other biomarkers, phenotypes, or physiological changes associated with a chymase-associated disease. For example, in asthma, it was recently reported that VEGF level and airway vascular permeability index was inversely correlated with degree of airway obstruction and airway hyperreactivity to methacholine in asthmatics (Kanazawa et al., *Clin Exp Allergy.* 2005 November; 35(11):1432-6). In particular, it was found that VEGF levels in induced sputum and airway vascular permeability index were significantly higher in asthmatics without ulcerative colitis (UC) and asthmatics with UC than in normal controls or UC patients (Id.). Thus, in a method of the present invention of diagnosing an asthmatic condition or a method of the present invention of evaluating the effectiveness of a treatment to an asthmatic condition, the method further comprises the step of analyzing the expression level of VEGF in induced sputum of the human subject.

Chronic obstructive pulmonary disease (COPD) is an inflammatory lung disease associated with progressive airflow limitations that is not fully reversible. COPD includes chronic obstructive bronchitis and emphysema, commonly associated with smoking. While the precise etiology of COPD is unknown, the medical literature suggests that in some instances, COPD may represent a pathological progression from very severe chronic asthma. Hence, the current therapies available for the treatment of COPD are primarily those designed to reduce the airway and lung inflammation associated with asthma. Current therapies include oral or inhaled corticosteroids and bronchodilators such as $\beta_2$-adrenergic agonists and cholinergic antagonists. One could therefore anticipate that a new therapy for asthma would also be a likely therapy for COPD. For reviews on COPD see: de Boer, W. I. Perspectives for cytokine antagonist therapy in COPD. *Drug Discovery Today*, 10(2):93, 2005; and Barnes, P. J. New Treatments for COPD. *Nature Reviews—Drug Discovery*, 1: 437, 2002. Like asthma, the inflammatory aspect of COPD can be characterized by an inflammatory response that includes an influx of white blood cells, such as neutrophils and macrophages, into the lungs and airways. This influx is one of the hallmarks of the airway and lung inflammation associated with both asthma and COPD. Thus, in a method of the present invention of diagnosing a COPD condition or a method of the present invention of evaluating the effectiveness of a treatment to a COPD condition, the method further comprises the step of measuring the influx of white blood cells into the lungs and airways.

Cytokines are key inflammatory mediators in asthma and COPD. Pro-inflammatory cytokines include, among others, interleukin (IL)-1, tumor necrosis factor (TNF)-$\alpha$ and macrophage chemotactic factor (MCP)-1. Effective therapeutic agents for the treatment of asthma and COPD tend to reduce levels of these pro-inflammatory cytokines. Thus, in a method of the present invention of diagnosing an asthma or a COPD condition or a method of the present invention of evaluating the effectiveness of a treatment to an asthma or a COPD condition, the method further comprises the step of measuring the level of cytokines in the subject.

Another aspect of the present invention is a method of classifying patients who have a better chance to respond to chymase inhibitor treatment, comprising the step of measuring the level of SLPI cleavage in such patients. A patient with more cleavage of SLPI is likely to have hyperactive chymase, and thus likely to be more responsive to the chymase inhibitor therapy. For example, asthma may be produced by constriction-related (application of bronchial dilators) and/or air-way construction-related (mucus over production) activities. It remains to be determined if the role of mast cells and its released chymase is involved in either or both of the aberrant pathophysiological features of asthma. Hence, asthma could be the result of chymase-dependent and/or chymase independent mechanisms. To that end, the specific cleavage of SLPI by chymase can be used to associate or validate or stratify chymase-dependent from chymase-independent asthmatic populations to strengthen chymase inhibitor efficacy performance.

The present invention further provides a method of identifying a compound that decreases the biological activity of a human chymase comprising the steps of: a) contacting a test compound with a human chymase and a human SLPI in an assay mixture; b) incubating the assay mixture under a condition wherein the human chymase cleaves the human SLPI; c) measuring the level of a human SLPI fragment resulting from the chymase cleavage in the assay mixture; and d) comparing the amount detected from step c) to that detected from a control, wherein the test compound is omitted from the assay mixture.

The compound identification methods can be performed using conventional laboratory formats or in assays adapted for high throughput. The term "high throughput" refers to an assay design that allows easy screening of multiple samples simultaneously and/or in rapid succession, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, greater numbers of samples can be processed using the design of the present invention.

Any test compounds may be screened in the screening assays of the present invention to select modulators of the protein complex of the invention. By the term "identifying" compounds it is intended to encompass both (a) choosing compounds from a group previously unknown to be modulators of chymase; and (b) testing compounds that are known to be capable of binding, or modulating the functions and activities of chymase. Both types of compounds are generally referred to herein as "test compounds" or "candidate compounds". The candidate compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes, and derivatives, mimetics and analogs thereof. Preferably, they are small organic compounds, i.e., those having a molecular weight of no greater than 10,000 daltons, more preferably less than 5,000 daltons. Preferably, the test compounds are provided in library formats known in the art, e.g., in chemically synthesized libraries (See generally, Gordan et al. *J. Med. Chem.*, 37:1385-1401 (1994)), recombinantly expressed libraries (e.g., phage display libraries), and in vitro translation-based libraries (e.g., ribosome display libraries).

Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of chymase activity. Therefore, a source of candidate agents is one or more than one library of molecules based on one or more than one known compound that increases or decreases chymase activity in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing compounds.

A variety of other reagents also can be included in the mixture. These include reagents such as salts, buffers, neutral proteins (e.g., albumin), detergents, etc. that can be used to facilitate optimal protein-protein and/or protein-nucleic acid binding. Such a reagent can also reduce non-specific or background interactions of the reaction components. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J. Med. Chem.* 37:2678. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,571,698), plasmids (Cull et al. (1992) *Proc. Natl. Acad. Sci. USA* 89:1865-1869) or phage (see e.g., Scott and Smith (1990) *Science* 249:3 86-390).

The selected compounds can be tested for their ability to decrease the biological activity of chymase to cleave a SLPI at the specific site Leu72-Met73. During the test, the test compound can be added to the chymase prior to, after, or simultaneously with SLPI that serves as the substrate for SLPI protease activity. Generally, a control assay is performed in which the above screening assay is conducted in the absence of the test compound. The result of this control assay is then compared with that obtained in the presence of the test compound.

The chymase or the SLPI in the screening assay can be isolated or not isolated. In one embodiment, substantially purified chymase or SLPI can be used in the screening assay. It will be apparent to skilled artisans that any recombinant expression methods may be used in the present invention for expression and purification of SLPI or chymase. Exemplary nucleic acid molecules that can be used in the present invention include nucleic acid molecules that encode the human chymase or SLPI.

Typically, the nucleic acids, preferably in the form of DNA, are incorporated into a vector to form expression vectors capable of directing the production of the interacting protein member(s) once introduced into a host cell. Many types of vectors can be used for the present invention. Methods for the construction of an expression vector for purposes of this invention should be apparent to skilled artisans apprised of the present disclosure. (See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D. C., Ch. 3, 1986; Bitter, et al., in *Methods in Enzymology* 153:516-544 (1987); *The Molecular Biology of the Yeast Saccharomyces*, Eds. Strathern et al., Cold Spring Harbor Press, Vols. I and II, 1982; and Sambrook et al., *Molecular Cloning: A Laboratory Manual*, Cold Spring Harbor Press, 1989.)

Generally, the expression vectors include an expression cassette having a promoter operably linked to a DNA encoding an interacting protein member. The promoter can be a native promoter, i.e., the promoter found in naturally occurring cells to be responsible for the expression of the interacting protein member in the cells. Alternatively, the expression cassette can be a chimeric one, i.e., having a heterologous promoter that is not the native promoter responsible for the expression of the interacting protein member in naturally occurring cells. The expression vector may further include an origin of DNA replication for the replication of the vectors in host cells. Preferably, the expression vectors also include a replication origin for the amplification of the vectors in, e.g., *E. coli*, and selection marker(s) for selecting and maintaining only those host cells harboring the expression vectors.

The thus constructed expression vectors can be introduced into the host cells by any techniques known in the art, e.g., by direct DNA transformation, microinjection, electroporation, viral infection, lipofection, gene gun, and the like. The expression of the protein of interest may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. In stable cell lines, at least the expression cassette portion of the expression vector is integrated into a chromosome of the host cells.

The vector construct can be designed to be suitable for expression in various host cells, including but not limited to bacteria, yeast cells, plant cells, insect cells, and mammalian and human cells. Methods for preparing expression vectors for expression in different host cells should be apparent to a skilled artisan.

Homologues and fragments of chymase or SLPI can also be easily expressed using the recombinant methods described above. For example, to express a protein fragment, the DNA fragment incorporated into the expression vector can be selected such that it only encodes the protein fragment. Likewise, a specific hybrid protein can be expressed using a recombinant DNA encoding the hybrid protein. Similarly, a homologue protein may be expressed from a DNA sequence encoding the homologue protein. A homologue-encoding DNA sequence may be obtained by manipulating the native protein-encoding sequence using recombinant DNA techniques. For this purpose, random or site-directed mutagenesis can be conducted using techniques generally known in the art. To make protein derivatives, for example, the amino acid sequence of a native interacting protein member may be changed in predetermined manners by site-directed DNA mutagenesis to create or remove consensus sequences.

In another embodiment, the chymase or SLPI involved in the present invention can be present in a biological sample, such as saliva, sputum, nasal exudate, ELF, and lavage fluids etc. The chymase or SLPI can also be associated with a cell or present in a cell lysate.

The method of the present invention further comprises the step of testing the compound in one or more other assays for the chymase activity. The compounds can be further tested for the other activities of chymase, including but not limited to, its ability to convert angiotensin I to the vasoactive peptide angiotensin II, to selectively convert big endothelin 1 to the 31 amino acid length peptide endothelin 1, to degrade the extracellular matrix, to cleave stem cell factor to yield a bioactive, soluble product, to process procollagenase, inflammatory cytokines and other bioactive peptides, etc. In a particular embodiment, the compounds can be further tested in an enzyme inhibition assay involving a chymase and a chromogenic substrate (see for example, Garavilla et al., *The J. Bio. Chem.* 2005, 280:18001-18007).

The method of the present invention further comprises the step of testing the compounds in an animal model for the chymase-associated diseases. For example, a well-accepted model of airway inflammation is the *Ascaris suum* antigen-induced asthmatic sheep model. After administering a test compound to the sheep model, a reduction in the influx of neutrophils and macrophages would suggest to one of ordinary skill in the art that the compound would be useful for the treatment of the airway and lung inflammation associated with both asthma and COPD. Another model of airway inflammation is lipolysaccharide (LPS)-induced airway neutrophilia in rats, where, upon introduction of LPS into the lungs, there is an influx of white blood cells into the bronchoalveolar lavage fluid. After administering a test compound to the rat mode, reversed LPS-induced airway inflammation, and lowered neutrophil counts in the bronchoalveolar lavage fluid, would suggest to one of ordinary skill in the art that the test compound would be useful for the treatment of both asthma and COPD. Yet another model for asthma and COPD is a model of glycogen-induced acute peritonitis in rats. After administering a test compound to the rat mode, reduced levels of pro-inflammatory cytokines include, among others, IL-1, TNF-α, and MCP-1, in the ascites fluid and plasma of glycogen-treated rats would demonstrate that the test compound would be useful for the treatment of both asthma and COPD.

Example 1

Human Chymase Cleaved Recombinant Human SLPI at a Specific Site

Although human SLPI cleavage by bovine (Grutter et al., Embo J 1988; 7:345-51) and ovine (Pemberton et al., Biochim Biophys Acta 1998; 1379:29-34) mast cell proteases has been reported by investigators, no investigation of SLPI cleavage by human chymase has been reported. This Example investigated the ability of human chymase to cleave recombinant human SLPI (rSLPI).

Recombinant human SLPI and goat anti-SLPI polyclonal antibody were obtained from R&D systems (Minneapolis, Minn.). Rabbit anti-SLPI antibody was obtained from Abcam (Cambridge, Mass.). Human chymase and tryptase were obtained from Cortex Biochem (San Leandro, Calif.). Cathepsin G and elastase were purchased from Biodesign International (Saco, Me.) and Proteinase 3 was purchased from Fitzgerald Industries International (Concord, Mass.). Unless otherwise indicated, similar reagents were also used in the other Examples included herein.

Recombinant human SLPI was incubated with human chymase (molar ratio 40:1) in 0.1 M Tris-HCl, pH 8.0, 0.5 M NaCl at 37° C. Samples were collected after various time points. Reduced samples were separated on a 4-12% SDS-PAGE (NuPAGE, Invitrogen) (2 ug rSLPI per well) and stained with Coomassie stain.

Figure 1:
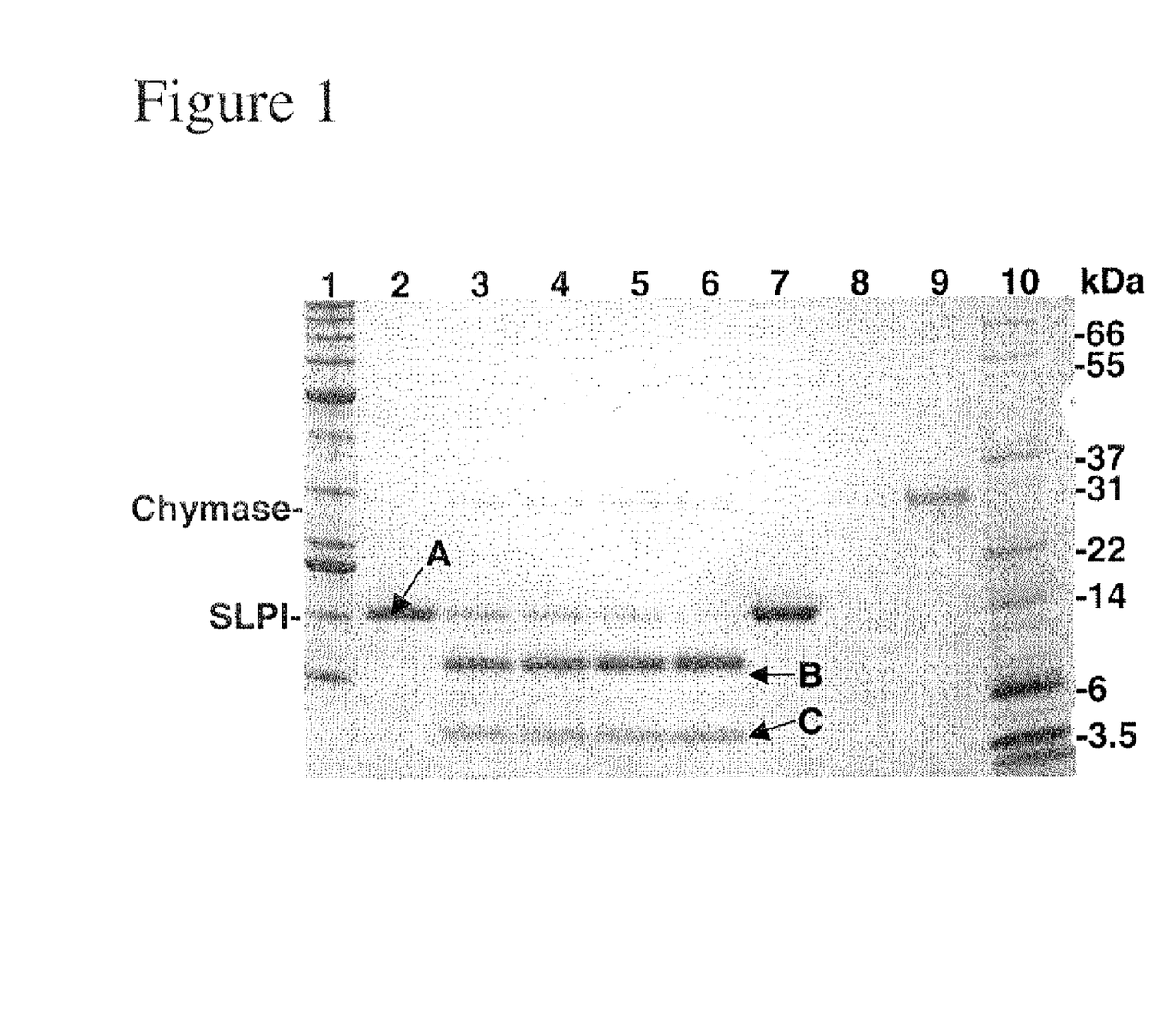
FIG. 1 shows the digestion of recombinant human SLPI (rSLPI) by human chymase. The samples at each lane are: 1—Protein size standard (BechMark, Invitrogen); 2—SLPI, 0 h; 3—Chymase+SLPI, 20 min; 4—Chymase+SLPI, 140 min; 5—Chymase+SLPI, 4 h; 6—Chymase+SLPI, 21 h; 7—SLPI, 21 h; 8—Chymase 21 h; 9—1 ug Chymase; 10—Protein size standard (Mark-12, Invitrogen).

FIG. 1 shows that cleavage of recombinant human SLPI was observed after rSLPI was incubated with human chymase for about 20 minutes. Even in a ten-fold excess of rSLPI to chymase most of the rSLPI protein was cleaved (data not shown). The full length human SLPI was cleaved into two fragments. Mass spectrometry analyses indicated that the about 11.7 kD full length human SLPI was cleaved into two fragments of the sizes approximately of 7.9 and 3.8 kD. To determine the exact site of cleavage, N-terminal sequencing was performed on the full length (FIG. 1, band A) and cleaved bands (FIG. 1, bands B and C). Sequencing analysis indicated that the cleavage of recombinant human SLPI by human chymase was at Leu72-Met73. This result showed that SLPI, a known inhibitor of chymase (Fink et al., Biol Chem Hoppe Seyler 1986; 367:567-71), acted also as a substrate of chymase. This was consistent with the activity of the bovine and ovine mast cell proteases on the cleavage of human SLPI (Grutter et al., supra; and Pemberton et al., supra).

A panel of proteases including elastase, cathepsin G, tryptase and proteinase 3 was tested for their ability to cleave the recombinant human SLPI using LC/MS analysis. These proteases were known to be inhibited by SLPI. Recombinant human SLPI (1 μg) was incubated for 5 hours with a test protease (50 ng). Samples were then diluted in 50 mM $NH_4HCO_3$ buffer to about 0.1 g protein/L. Liquid Chromatography was performed using an Agilent 1100 LC/MSD. The diluted sample (10 μL) was injected on a Zorbax SB300 5u C8, C18 (150×2.1 mm) column at a flow rate 0.2 mL/min. Proteins within the sample were eluted using a 30 minute gradient from 15% to 60% solvent B in solvent A, wherein Solvent A: (0.1% Formic acid+0.02% TFA)/$H_2O$; and Solvent B: (0.1% Formic acid+0.02% TFA)/ACN. Cleaved rSLPI was detected at a retention time of 10.7 minutes while the intact SLPI was detected at 12.2 minutes. The Agilent 1100 MSD SL mass spectrometer was interfaced with an 1100 HPLC system through an electrospray ionization source. Chemstation software version 10.02 was used for the system control and data acquisition.

From LC/MS, the native rSLPI was isolated and detected at the expected size of 11708 daltons. After incubation with chymase a second peak was resolved from the HPLC. This second peak had an additional 18 mass units, consistent with the addition of water to the nicked or cleaved rSLPI molecule. Thus, the presence of the second peak indicated that chymase indeed cleaved rSLPI, as was observed from the SDS-PAGE analyses. Incubation of rSLPI with the other proteases on the panel did not result in the formation of the second peak, indicating that the other proteases tested did not cleave the rSLPI. Reduction of the rSLPI samples in the presence of the proteases did result in cleavage of the SLPI protein, indicating that the other proteases were able to cleave the reduced form of rSLPI.

The inability of other proteases to cleave SLPI is consistent with the studies of Vogelmeier et al., which showed no cleavage of SLPI by elastase and cathepsin G (*J Clin Invest* 1991; 87:482-8).

Example 2

Chymase Inhibitors Decreased the Cleavage of Human rSLPI by Human Chymase

This Example examines the effect of chymase inhibitors on the cleavage of human SLPI by the human chymase. Two chymase inhibitors were tested at various concentrations: chymase inhibitor A, [2-(3-{Methyl-[1-(naphthalene-2-carbonyl)-piperidin-4-yl]-carbamoyl}-naphthalen-2-yl)-1-naphthalen-1-yl-2-oxo-ethyl]-phosphonic acid), which has been described in US20030195172; and chymase inhibitor B, {(5-Chloro-benzo[b]thiophen-3-yl)-[2-(3-chloro-5-fluoro-phenyl)-vinylcarbamoyl]-methyl}-methyl-phosphinic acid, which has been described in US20050176769.

Recombinant human SLPI (80 pmoles) was incubated with human chymase (80 pmoles) in the presence or absence of chymase inhibitors for 30 minutes at 37° C. in either 1M Tris buffer (pH 7.5) or PBS. Western Analysis was performed to quantify the amount of the rSLPI and the amount of the larger cleavage product of SLPI (about 7.9 kD from mass spectrometry analyses). The samples were denatured and reduced with an equal volume of buffer containing SDS and beta-mecaptoethanol. Each sample was applied to a 4-20% gradient polyacrylamide gel or a 15% polyacrylamide gel. The samples were electrophorezed and transferred to a PVDF membrane (Pierce Biotechnology, Rockford, Ill.). The blots were blocked in 5% milk/PBS-tween (PBS/0.4% tween-20) for 1 hour at room temperature. The blots were incubated overnight at 4° C. in the primary antibody (goat anti-SLPI at 1:1000 or rabbit anti-SLPI at 1:2000) diluted in blocking solution. After three washes of PBS-tween the blot was incubated for 1 hour at room temperature with the secondary antibody (goat anti-rabbit HRP or rabbit anti-goat HRP) diluted 1:2500 in blocking solution. The blots were washed 6 times with PBS-tween and incubated for 1 minute at room temperature with Wester Lightning chemiluminescence reagents (Perkin Elmer, Boston, Mass.) and developed on Biomax Light Film (Eastman Kodak, Rochester, N.Y.) in the darkroom. A densitometer, Fluor Chem™ 8000, Advanced Fluorescence, Chemiluminescence and Visible Imaging System from Alpha Innotech (San Leandro, Calif.), was used to measure the densities correlated to the amount of the rSLPI and the amount of the larger cleavage product of SLPI on the developed film.

The percentage of SLPI cleavage was calculated with the formula: 100×(density of the larger SLPI cleavage product/(density of the rSLPI+density of the larger SLPI cleavage product)).

Figure 2:
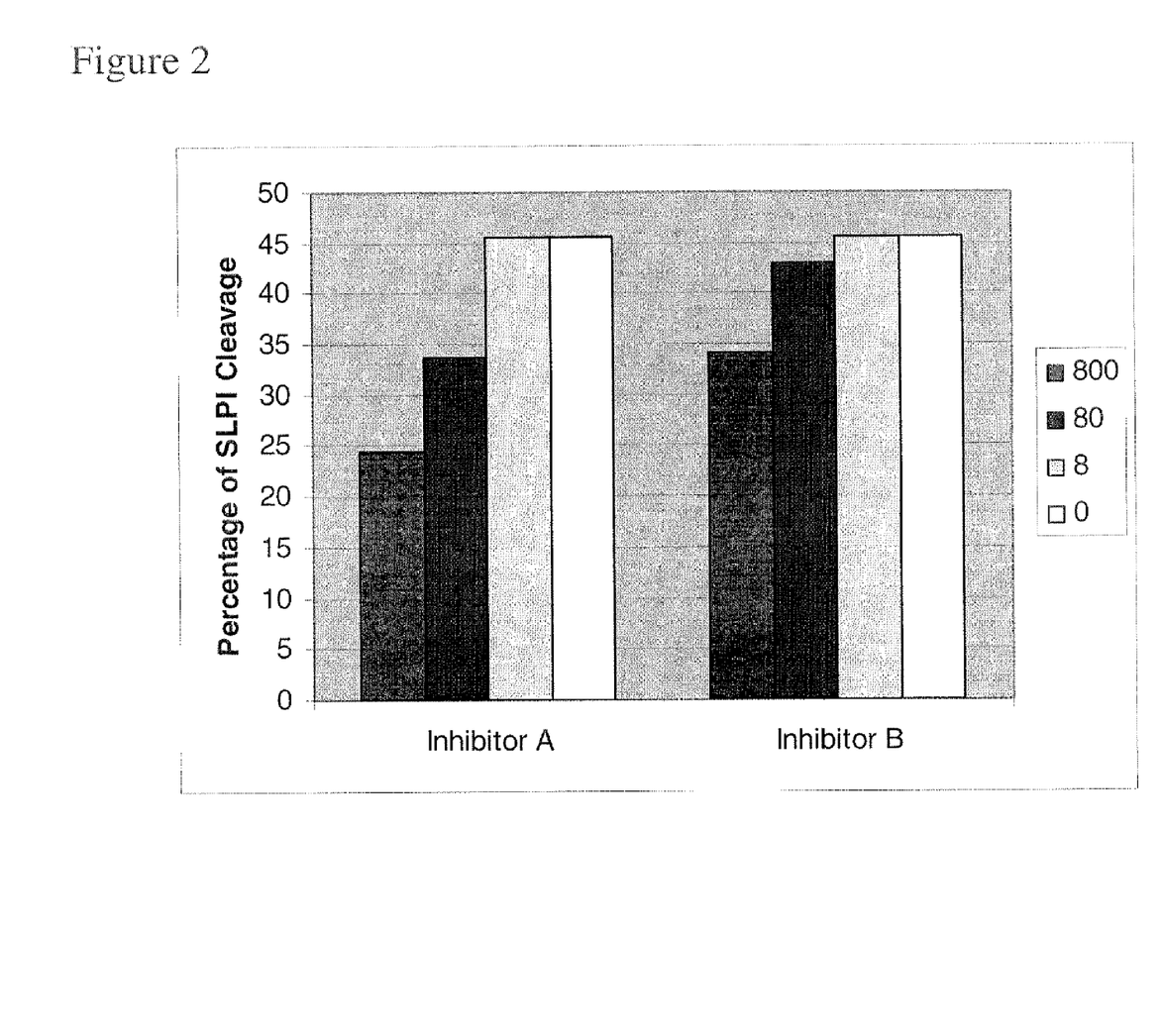
FIG. 2 illustrates that known chymase inhibitors decreased the cleavage of rSLPI by chymase. The numbers 0, 8, 80, 800, indicate the amount of chymase inhibitor present in the assay mixture in the unit of pmoles.

FIG. 2 shows the effects of the chymase inhibitor on the cleavage of SLPI by chymase. The amount of inhibition was directly related to the amount of chymase inhibitor added. This suggested the usefulness of this assay for determining the efficacy of chymase inhibitor compounds.

Example 3

Human Chymase Cleaved Human SLPI in a Clinical Sample

This example illustrates an ex vivo assay to determine SLPI cleavage from an easily accessible clinical sample, human saliva.

Ten μl of human saliva was incubated with chymase (4 μg/0.1 U/5 μM) and/or chymase inhibitor (100 μM) brought up to a total volume of 30 μl with PBS for 30 min at 37° C. For undigested saliva samples 10 μl of saliva were diluted in 20 μl of PBS. As described in Example 2, Western analysis was performed to determine the amount of SLPI and the amount of the larger SLPI cleavage product in the saliva sample, and the percentage of SLPI cleavage was calculated.

Figure 3:
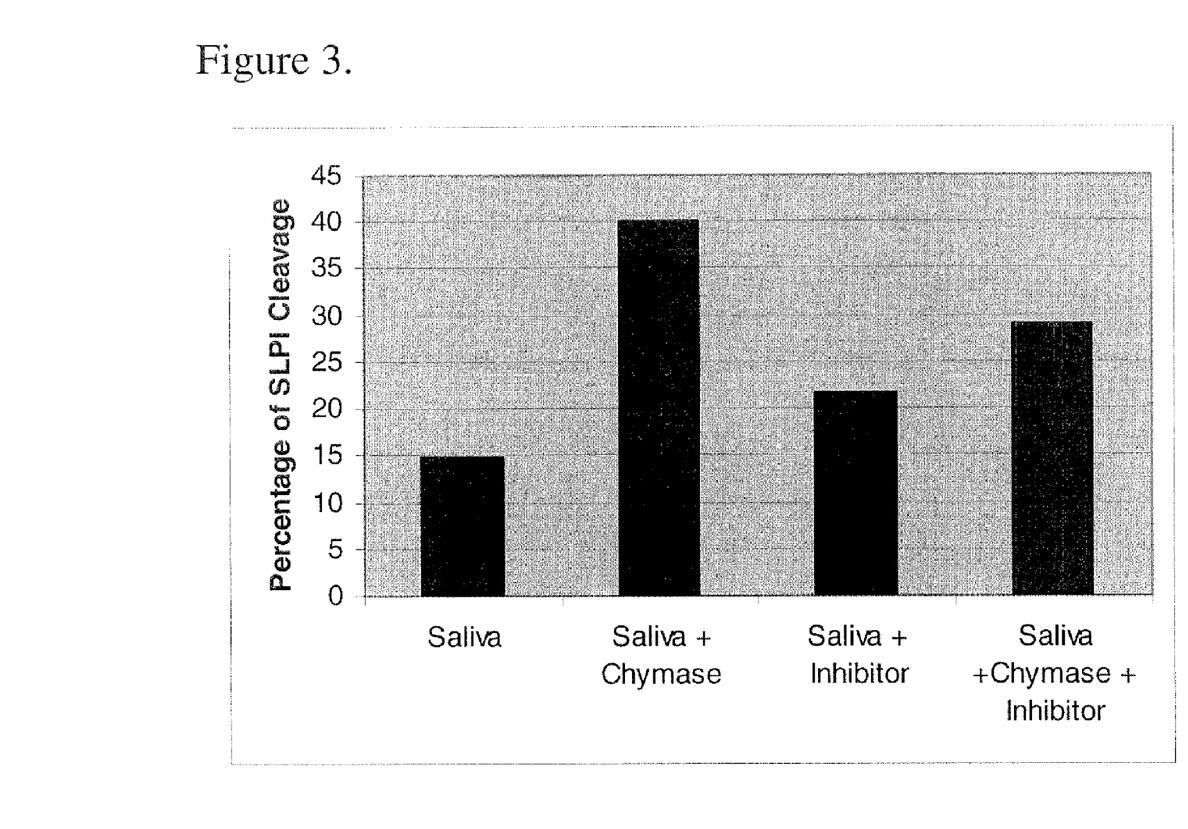
FIG. 3 illustrates that chymase was able to cleave SLPI present in samples of human saliva, and that chymase inhibitor reduced the cleavage.

FIG. 3 shows that exogenous chymase cleaved SLPI in the saliva sample as it did with the rSLPI. It also shows the effect of a chymase inhibitor on the ability of chymase to cleave SLPI. The chymase inhibitor, {(5-Chloro-benzo[b]thiophen-3-yl)-[2-(3,4-difluoro-phenyl)-vinylcarbamoyl]-methyl}-methyl-phosphinic acid, has been described in US20050176769. The inhibitor decreased chymase activity and inhibited the cleavage of SLPI from saliva (FIG. 3). These results indicated that the activity of chymase as well as the efficiency of chymase inhibitors can be monitored from the saliva samples.

Consistent with the results of Example 1, among the panel of proteases tested, the cleavage of SLPI in saliva was unique to chymase. The larger SLPI cleavage product was not observed when the saliva samples were incubated with cathepsin G, tryptase and proteinase 3. Minor digestion of SLPI was observed after the saliva was incubated with elastase. However, the resulting digestion products, a doublet of bands (~11 and 10.5 kD after SDS-PAGE analyses), were different in size from the cleavage products resulting from chymase digestion.

Example 4

SLPI Processing as a Biomarker for Chymase-Associated Diseases

The cleavage of SLPI was measured in human saliva samples from normal subjects and patients with allergy, a disorder that is associated with hyperactivity of chymase.

Saliva samples were obtained from human subjects: one complaining of an allergic condition induced by exposure to mice (allergy), and the other having no respiratory ailments (normal). The samples were frozen and stored at −80° C. The samples were thawed on ice and vortexed. Saliva (10 μl) was diluted with PBS 15 (μl). As described in Example 2, Western analysis was performed to determine the amount of SLPI and the amount of the larger SLPI cleavage product in the saliva sample, and the percentage of SLPI cleavage was calculated.

Figure 4:
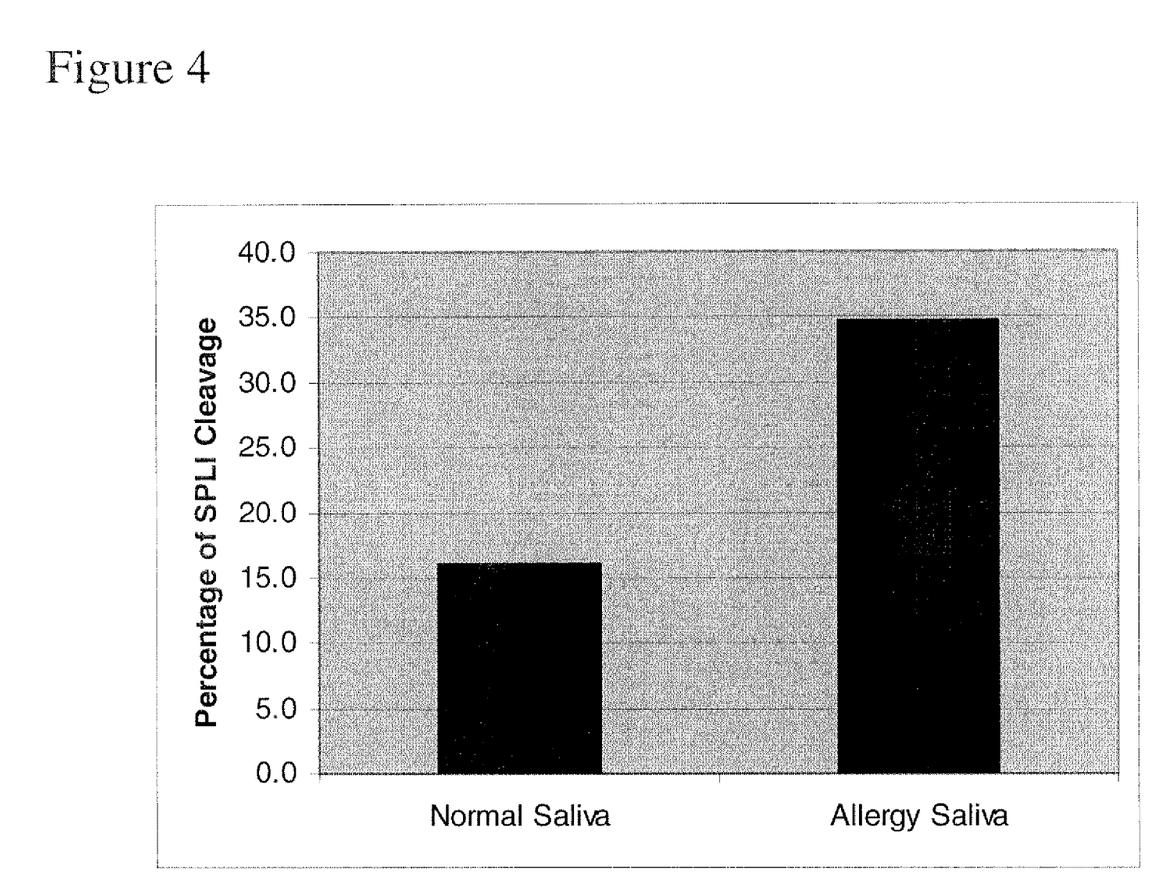
FIG. 4 compares the level of SLPI cleavage in saliva samples taken from a normal human subject and a patient with a chymase-associated disease.

FIG. 4 shows the differential amount of SLPI cleavage between saliva samples from normal subject and the patient with allergy. A higher percentage of SLPI cleavage was observed in the allergy saliva sample, indicating that SLPI processing can be used as a biomarker for chymase-associated diseases.

Example 5

The following methodology was employed to investigate the soluble components (mediators, cytokines) of the upper airway inflammation in the nose at baseline and in response to a relevant allergen in subjects with allergic rhinitis.

Materials
1 pipette (>10 cc) or 10 cc syringe
Sterile nasal wash solution: NaCl 0.9%, 10 ml for 1 nostril, preheated to 37° C.
Preheating device
Tissues
Funnel (40 mm)
Syringes (10 cc)
Plastic containers
Nasal speculum
Xylomethazoline 0.1% nasal spray on Ice
Method
(Modified from validated technique by De Graaf-In't Veld C, et at; Clin Exp Allergy 1995; 25:966-73)
1. A sterile solution of NaCl 0.9% is warmed to 37° C.
2. Accessibility of the nose is checked with a nasal speculum and sufficient light.
3. The subject extends its neck approximately 30° while seated. Instill ten (10) cc of a warmed-up NaCl 0.9% solution into one nostril with a pipette or syringe. Instruct subject not to swallow or to breathe during the procedure.
4. After 10 seconds, ask the subject to bend over and gently expel the wash fluid from its nose into a funnel (connected to 10 cc syringe).
5. Pre-challenge, employ 4 nasal washings in total, to get rid of debris.
6. To test reproducibility with study day 1, analyze the first wash-fluid on day 2 (pre-challenge); after the first nasal washing on day 2, spray 1 puff of xylomethazoline 0.1% in each nostril 10 min before the other 3 NAL procedures (do not allow subject to blow its nose).
7. Some minutes later, perform the $2^{nd}$ and 3rd nasal wash (and dispose of).
8. Store the 4th wash fluid in a plastic container on ice until processing.
9. Process all NALs within 1 h and until the time of processing stored on ice.

Figure 5A:
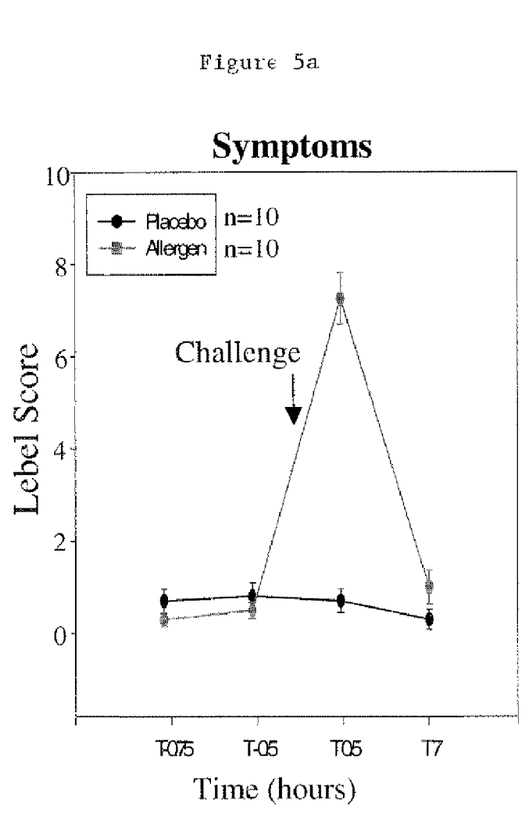
Figure 5B:
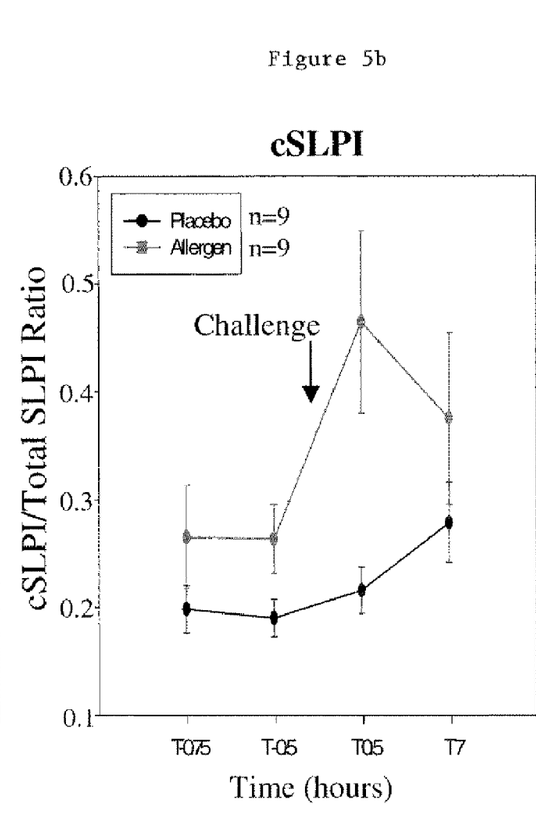

The results are shown in FIG. 5. FIG. 5 illustrates that an increase in cSLPI correlates with increase in allergic symptoms. cSLPI to total SLPI ratios were determined in nasal lavages by western analysis obtained from individuals 0.75 hours and 0.5 hours prior to antigenic challenge and 0.5 hours and 7 hours post antigen challenge (FIG. 5b). Patients were scored for symptom intensity (Lebel score) at the same time points (FIG. 5a).

Example 6

Sputum was collected from subjects using European Respiratory Society (ERS) recommendations, and protocols that consist of the inhalation of hypertonic or isotonic saline solution. In mild to moderate asthmatics sputum was induced with hypertonic saline which was aerosolised and inhaled for 3-4 5 min periods. In more severe asthmatics a modified ERS protocol was used beginning inhalation with normal saline and progressing more slowly moving to hypertonic saline only if there was no significant fall in $FEV_1$.

Figure 6:
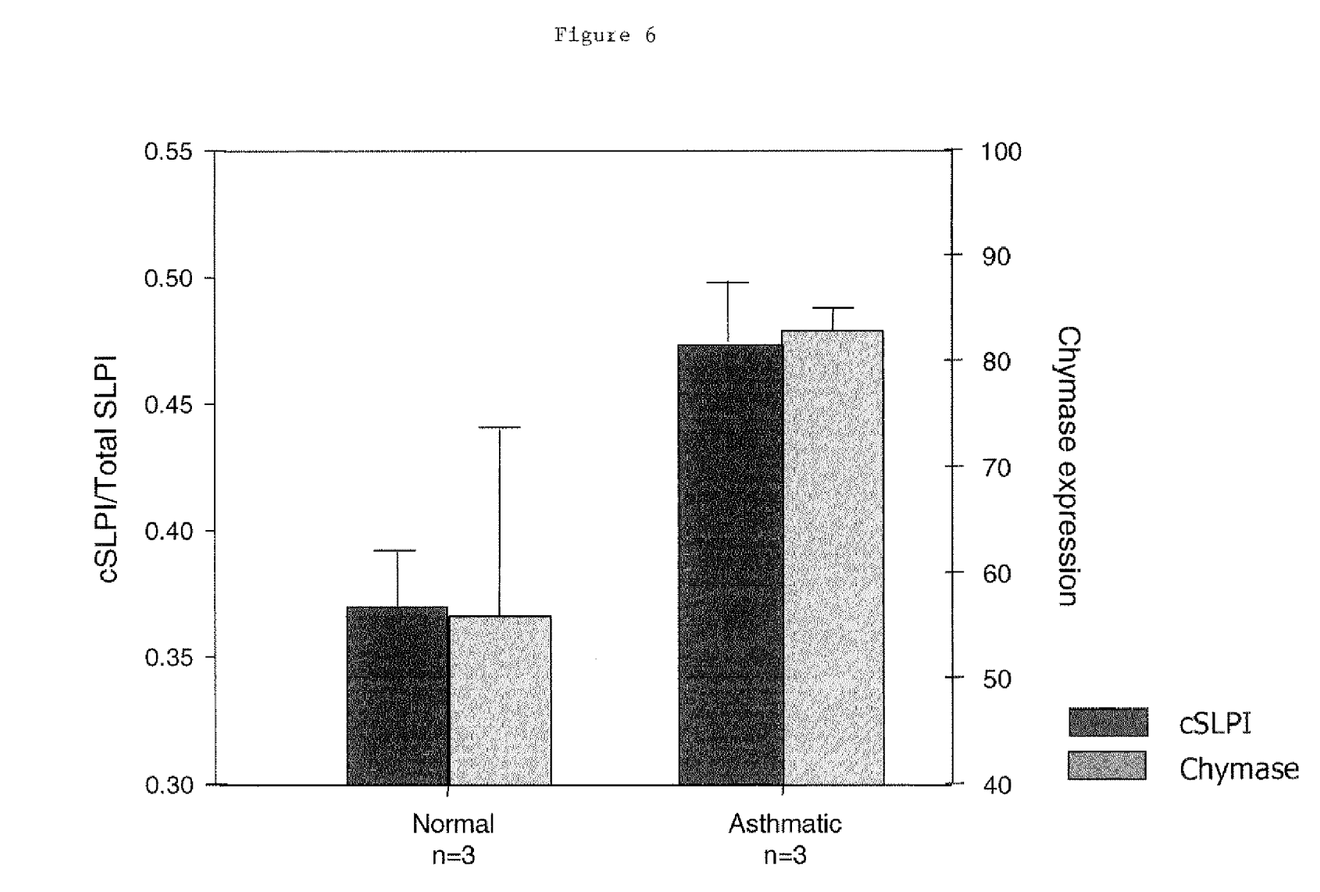
FIG. 6 illustrates that asthmatic sputum samples contain higher percent cSLPI/total SLPI than normal sputum samples and correlate with chymase levels from these individuals. Sputum samples were obtained from both normal and asthmatic subjects. Both cSLPI to SLPI ratios and chymase levels were determined by western analyses. Values were determined by densitometry analysis.

The results are show in FIG. 6. FIG. 6 illustrates that asthmatic sputum samples contain higher percent cSLPI/total SLPI than normal sputum samples and correlate with chymase levels from these individuals. Sputum samples were obtained from both normal and asthmatic subjects. Both cSLPI to SLPI ratios and chymase levels were determined by western analyses. Values were determined by densitometry analysis.

What is claimed is:

1. A method of detecting a chymase-associated disease in a human subject, comprising the steps of:
   a. obtaining a biological sample from the human subject;
   b. measuring the level of human Secretory Leukocyte Protease Inhibitor (SLPI) cleavage by human chymase in the biological sample, wherein the level of human SLPI cleavage by human chymase is measured as a ratio of a human SLPI fragment resulting from chymase cleavage to the full length SLPI present in the biological sample; and
   c. comparing the level measured from step b) to a control of the level of human SLPI cleavage by human chymase in a healthy human subject, wherein an elevated level of human SLPI cleavage by human chymase compared to said control indicates that the human subject has a chymase-associated disease or has increased risk of a chymase-associated disease.

2. The method of claim 1, wherein the biological sample is saliva.

3. The method of claim 1, wherein the chymase-associated disease is selected from the group consisting of asthma, allergic rhinitis, fibrosis, hypertension, cardiac hypertrophy, heart failure, rheumatoid arthritis, diabetic nephropathy, cystic fibrosis, COPD, and inflammatory diseases.

4. The method of claim 1, wherein the full length human SLPI comprises the amino acid sequence of SEQ ID NO: 1.

5. The method of claim 1, wherein the human SLPI fragment resulting from chymase cleavage consists essentially of the amino acid sequence of SEQ ID NO: 3.

6. The method of claim 1, wherein the human SLPI fragment resulting from chymase cleavage consists essentially of the amino acid sequence of SEQ ID NO: 4.

7. The method of claim 1, wherein the full length human SLPI consists essentially of the amino acid sequence of SEQ ID NO: 2.

8. A method of evaluating the effectiveness of a treatment to a chymase-associated disease in a human patient, comprising the steps of:
   a. obtaining a biological sample from the human patient;
   b. measuring the level of human SLPI cleavage by human chymase in the biological sample, wherein the level of human SLPI cleavage by human chymase is measured as a ratio of a human SLPI fragment resulting from chymase cleavage to the full length SLPI present in the biological sample; and
   c. comparing the level measured from step b) to a control of the level of human SLPI cleavage by human chymase in the human patient prior to the treatment, wherein a decreased level of human SLPI cleavage by human chymase compared to said control indicates that the treatment to a chymase-associated disease in said patient is effective.

9. The method of claim 8, wherein the biological sample is saliva.

10. The method of claim 8, wherein the chymase-associated disease is selected from the group consisting of asthma, allergic rhinitis, fibrosis, hypertension, cardiac hypertrophy, heart failure, rheumatoid arthritis, diabetic nephropathy, cystic fibrosis, COPD, and inflammatory diseases.

11. The method of claim 8, wherein the full length human SLPI consists essentially of the amino acid sequence of SEQ ID NO: 1.

12. The method of claim 8, wherein the human SLPI fragment resulting from chymase cleavage consists essentially of the amino acid sequence of SEQ ID NO: 3.

13. The method of claim 8, wherein the human SLPI fragment resulting from chymase cleavage consists essentially of the amino acid sequence of SEQ ID NO: 4.

14. The method of claim 8, wherein the full length human SLPI consists essentially of the amino acid sequence of SEQ ID NO: 2.

15. The method of claim 8, wherein the treatment to a chymase-associated disease in a human patient involves a compound that decreases the biological activity of chymase.

\* \* \* \* \*